United States Patent [19]
Behrens

[11] Patent Number: 5,334,192
[45] Date of Patent: Aug. 2, 1994

[54] TARGETING DEVICE FOR AN IMPLANT

[75] Inventor: Klaus F. A. Behrens, Rickling, Fed. Rep. of Germany

[73] Assignee: Homwedica GmbH, Schoenkirchen, Fed. Rep. of Germany

[21] Appl. No.: 828,397

[22] Filed: Jan. 30, 1992

[30] Foreign Application Priority Data

Jan. 30, 1991 [DE] Fed. Rep. of Germany ... 9101037[U]

[51] Int. Cl.$^5$ ............................................. A61F 2/32
[52] U.S. Cl. ........................................ 606/96; 606/98; 606/102
[58] Field of Search .................. 606/96, 97, 98, 86, 606/87, 88, 62

[56] References Cited

U.S. PATENT DOCUMENTS

| | | | |
|---|---|---|---|
| 3,814,089 | 6/1974 | Deyerle | 606/98 |
| 4,103,683 | 8/1978 | Neufeld | 606/96 |
| 4,465,065 | 8/1984 | Gotfried | 606/96 |
| 4,622,959 | 11/1986 | Marcus | 606/96 |
| 4,733,654 | 3/1988 | Marino | 606/98 |
| 4,865,025 | 9/1989 | Buzzi | 606/96 |
| 4,881,535 | 11/1989 | Sohngen | 606/98 |
| 4,911,153 | 3/1990 | Border | 606/98 |
| 4,913,137 | 4/1990 | Azer | 606/96 |
| 4,976,713 | 12/1990 | Landanger | 606/62 |
| 5,103,398 | 4/1992 | McQueen | 606/62 |

FOREIGN PATENT DOCUMENTS

| | | |
|---|---|---|
| 0273872 | 10/1987 | European Pat. Off. . |
| 3312250 | 4/1991 | Fed. Rep. of Germany . |
| 3538346 | 4/1991 | Fed. Rep. of Germany . |

*Primary Examiner*—Michael A. Brown
*Attorney, Agent, or Firm*—Peter C. Richardson; Lawrence C. Akers; Elizabeth O. Slade

[57] ABSTRACT

A targeting device for implant to be used for fractures having a head that has a device for retaining a nail that will be inserted into a medullary canal of a bone, a locking device for releasably fastening the nail to the device for retaining the nail. A targeting arm attached to the head of the nail, wherein the targeting arm has an axis and a free end and it extends substantially parallel to nail.

11 Claims, 2 Drawing Sheets

TARGETING DEVICE FOR AN IMPLANT

The present invention refers to a targeting device for an implant to be used for fractures particularly in the trochanteric and subtrochanteric region, said device comprising a head having a projection to retain a femur nail to insert in the medullary canal of a femur locking means to releasably fasten the femur nail to the projection, and comprising a targeting arm laterally attached to the head, the arm extending parallel to a nail attached to the head and having at least one targeting bore for receiving a drill sleeve, the targeting bore being adapted to be aligned to a proximate angularly inclined bore or to a distal transverse bore of the femur nail.

Implants to be inserted by means of targeting devices are known from EP-0 25 7118. A nail is inserted in the femur proximity and has at least one transverse bore for receiving of a bone screw. In the proximate area, the nail has a bore inclined to the axis of the nail for accomodating a femur neck nail having a thread for cooperating with the femur neck or the femur head. The femur neck nail is placed in the transverse bore for free axial movement. Locking means prevent a rotation of the neck nail while allowing the axial movement. At least one distal locking screw maybe accomodated by a distal transverse bore in order to fix the nail in axial and rotational direction. In order to meet the requirements of bone anatomy in particular, to accomodate the angle between the femur neck and the femur shaft, femur nails are used having a different angular orientation of the bore, wherein a suitable nail is selected by the surgeon after prior x-ray analysis. For meeting the bone anatomy the nail may have a slight curvature in the medial lateral area. Nevertheless the nail axis may be approximately defined to be straight.

It is known for the surgeon to use targeting devices of the kind mentioned above which have a head for the attachment of a femur nail and which allows an insertion and alignment of the nail by careful striking. By means of such an instrument it is possible to determine positions of the nail in the axial and rotational direction as well. After the positioning a target arm is threaded accurately on the head which has targeting bores aligned with the proximal sloped bore or the distal transverse bore, respectively, of the femur nail. For each selected nail a mating targeting arm has to be attached, with the targeting bore corresponding to the angle of the bore. A known set of instruments needs 4 different targeting arms having transverse bores with different angles with respect to the axis of the targeting arm. Such a device has the disadvantage of expensive handling and may lead to errors. The device consists of a plurality of parts and, thus, is costly. Further, clearances may result from the many connections necessary which causes an imprecise setting of the femur neck nail or bone screws.

According to the object of the invention, an inexpensive targeting device is to be designed which can be handled more simply and which leads to more precise results.

According to the invention the targeting arm which is preferably attached to the head has a plurality of targeting bores extending at different angles with respect to the axis of the am to be aligned with differently oriented oblique bores of femur nails.

If the targeting arm is rigidly fixed to the head a rigid structure is achieved which allows a precise alignment of the drill sleeves with the inclined bores and the transverse bores. Therefore, the device according to the invention allows a precise placing of the femur neck and locking screws. The device according to the invention includes targeting bores which extend at different angles with respect to the axis of the targeting arm in order to achieve an adaptation to the nail selected to conform with the anatomy of the bone. In correspondence with the femur nail a suitable targeting bore can be selected for the orientation and insertion of the drill sleeve with respect to the inclined bore of the femur nail. The selection and mounting of different targeting arms is eliminated so that the handling of the device is considerably simplified and failures are avoided.

According to an embodiment of the invention the targeting bores include angles of 125°, 130°, 135° and 140° with respect to the arm axis, meeting the usual anatomic conditions.

According to a further embodiment of the invention the targeting bores for an inclined bore and a distal transverse bore of a femur nail may cross each other. This allows the arrangement of a plurality of targeting bores in the targeting device with relatively small dimensions.

According to a further embodiment of the invention the targeting arm has a clamping slot extending from the free end of the targeting arm and crossing the targeting bores to fix a drill sleeve (for the accomodation of a specific drill tool for the neck screw and the locking wall bone screws). It is desired to easily introduce the drill sleeve in one of the targeting bores so that the cross sectional areas of the targeting arm separated by the clamping slot usually have to be clamped against each other for fixing the drill sleeve. Preferably the clamping slot extends only along a portion of the cross section of the targeting arm so that the easy insertion of a drill sleeve is not worsened by an extreme flexibility of the targeting arm in the area of the bores.

According to a preferred embodiment of the invention a sleeve for covering the targeting bores has a first wall portion which can be locked to a second wall portion under a biasing force wherein the first wall portion presses legs of the targeting arm on either side of a clamping slot, and the sleeve has through-bores mating the targeting bores. The sleeve is placed on the targeting arm from the free end thereof and thereafter the drill sleeve can be introduced into the through-bores and targeting bores. Finally, the cross section of the targeting arm can be compressed in the area of the clamping slot by locking of both wall portions whereby the drill sleeve is fixed to the targeting arm.

According to a further embodiment of the invention the targeting arm has an approximately rectangular cross section and the sleeve has a corresponding box-shaped cross section, wherein the first and the second wall portions define perpendicularly oriented sleeve walls, and the first wall portion is bent away from the center of the sleeve with its side extending from a further sleeve wall, the free edge thereof being adapted to form a snapping connection with a separate sleeve wall of the second wall portion. Such a sleeve can be simply made of resilient plastic or metal.

According to a further embodiment of the invention a plurality of sleeves is provided adapted to be pushed on the targeting arm in the area of the targeting bores each thereof having only one through-bore for one of the different targeting bores of a targeting arm for inclined bores and possibly at least one through-bore for a targeting bore of a targeting arm for a transverse bore. The sleeve has to be selected in accordance with the selected femur nail having a specific orientation of this inclined bore, the sleeve allowing an introduction only in the corresponding targeting bore through its through-bore.

According to a further embodiment of the invention the head and the targeting arm are firmly interconnected by a retaining fend transparent to x-rays. This allows a position analysis of the nail and the femur neck screw. The transparent material may be made of carbon fibres or a similar plastic. Preferably, the head and the targeting arm may be of light metal, preferably of an aluminium or titanium alloy which facilitates the handling of the targeting device.

Finally, according to a further embodiment of the invention, the head has two approximately parallel guide bores for inserting laterally extending Kirschner-wires for a position control by x-rays, the guide bores extending in the plane defined by the targeting arm and the axis of the projection approximately perpendicular to the axis of the projection. If the Kirschher-wires are aligned with each other in the receiving plane of the x-rays (lateral medial direction) it is guaranteed that the central axis of the x-rays lies in the plane of the femur nail and the targeting arm.

Further details and advantages of a subject of the invention can be derived from the description below referring to the associated drawings showing a preferred embodiment of the device according to the invention.

Figure 1:
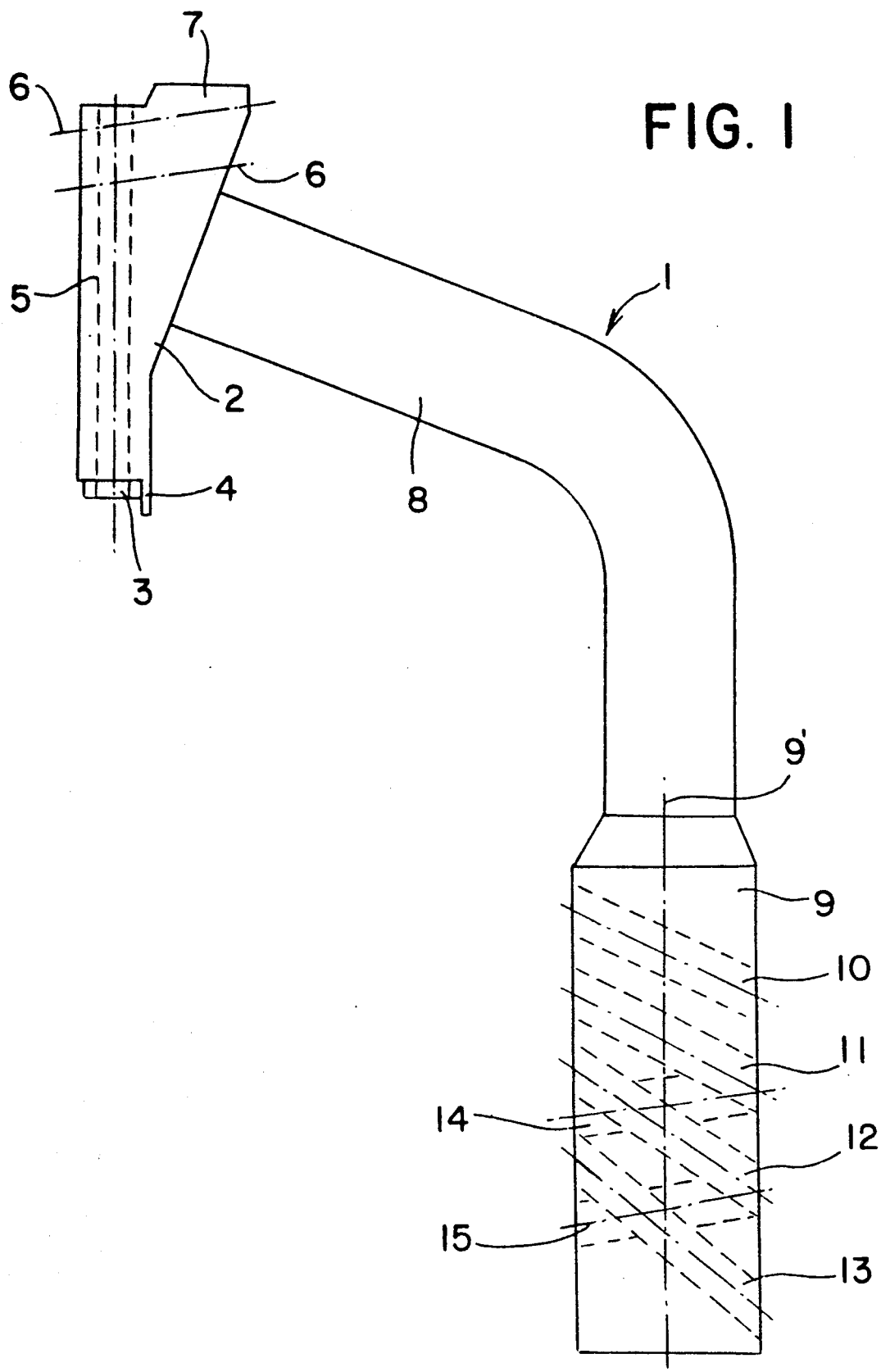
FIG. 1 is a side view of a targeting device.

According to FIG. 1, the targeting device 1 has a head 2 which includes a plug 3 at the lower end for applying a femur nail. Adjacent the plug 3 there is a nose 4 to accomodate a corresponding recess of the femur nail to secure the femur nail against rotation. The head 2 has a bore 5 through which a locking screw may be introduced to fix the femur nail to plug 3.

Two parallel guide bores 6 having a relatively small diameter for receiving socalled Kirschner-wires extending in the drawing plane and are provided in the upper area of the head 2. The upper guide bore 6 intersects partially a projection 7 provided for a striking tool.

Head 2 is fixedly secured to a targeting arm 9 through a retaining bent of a material transparent for x-rays. The longitudinal axis 9' of the targeting arm 9 extends approximately parallel to the axis of plug 3 and thus to the axis of a femur nail attached to plug 3.

The targeting arm 9 has first targeting bores 10, 11, 12, 13 having different angles with respect to the axis 9' of the targeting arm 9 namely 125°, 130°, 135° and 140°. This serves to receive a drill sleeve for a drill tool wherein the targeting bore 10, 11, 12, 13 is selected in accordance with the orientation of the angular bore in the femur nail in turn selected in accordance with the anatomic circumstances.

The targeting arm 9 has second targeting bores 14, 15 for receiving a drill sleeve to be aligned to distal transverse bores of the femur nail. Normally, each femur nail has two distal transverse bores which are positioned at the same location for all nail types. Targeting bores 11, 12 for oblique bores of the femur nail are crossing targeting bores 14, 15 for transverse bores of the femur nail in the lower region of the targeting arm 9.

Figure 2:
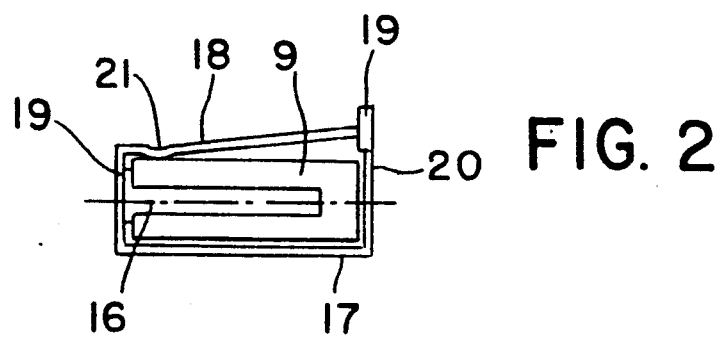
FIG. 2 is a bottom view of the targeting device of FIG. 1 with a sleeve pushed thereon.

As can be seen from FIG. 2 the targeting arm 9 has a longitudinal slot 16 starting from the free end thereof and extending to the side facing the femur nail to be fastened. The tongue-shaped cross sectional areas of the targeting arm 9 adjacent the clamping slot 16 can be resiliently pressed together to obtain thereby fixing a drill sleeve in one of the targeting bores 10 to 15.

To accomplish this a sleeve 17 having a box-shaped profile is pushed onto the targeting arm 9, the upper wall 18 of the sleeve 17 is connected to the sleeve wall 19 adjacent the slotted side of the targeting arm 9. The opposite end of the sleeve wall 18 is free and slightly bent away from the targeting arm 9 in a released state. It can be snapped under a projection 19' on the opposite sleeve wall 20 under a biasing force and thus locked. In the locked position an indentation 21 extending parallel to the axis of the targeting arm compresses the targeting arm in the area of the clamping slot 16 whereby the drill sleeve (not shown) is fixed. The lateral sleeve walls 19, 20 have through bores (not shown) for a drill sleeve.

Figure 3:
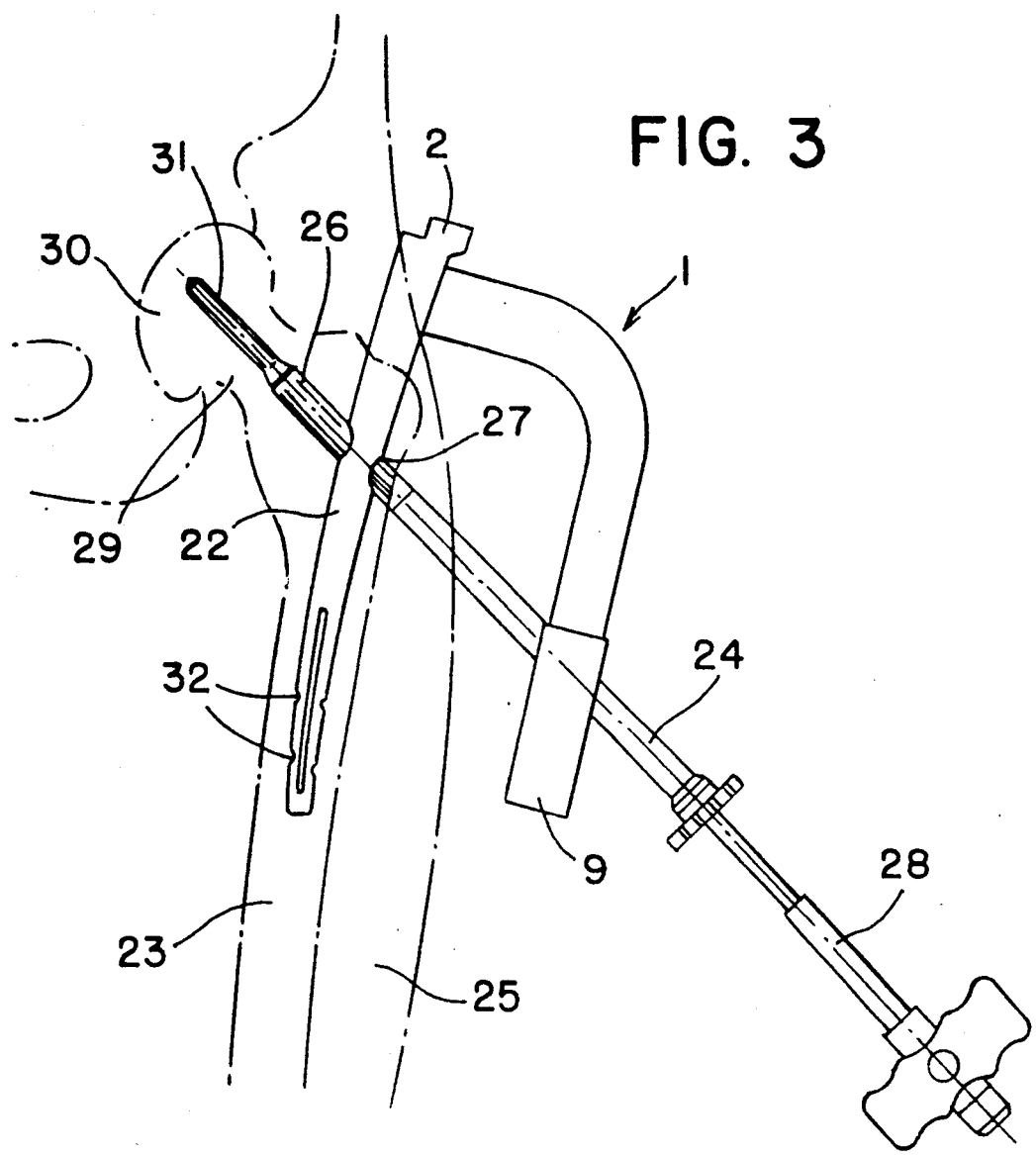
FIG. 3 is a side view of the targeting device of FIG. 1 showing additionally the introduction of a neck nail through a femur nail.

FIG. 3 illustrates the targeting device 1 with a femur nail 22 being attached to the head 2, the femur nail being already inserted in the medullary canal of a femur 23. A drill sleeve 24 is pushed into a targeting bore of the targeting arm 9 and fixed therein. The drill sleeve 24 is pressed into the soft tissue 25 and into the femur 23. For this purpose, the front end of the sleeve may have teeth also allowing a fixation to the bone. A femur neck screw 26 is slid through the drill sleeve 24 and through a sloped bore 27 of the femur nail. The screw 26 having a thread 31 at the forward position thereof is turned into the neck 29 and the femur head 30 by using a special rotary tool. In the position shown the femur neck screw 26 can be secured by a set screw (not shown) allowing an axial displacement thereof, however, preventing a rotation.

If necessary, the bore sleeve 24 can be pushed in one of the targeting bores in a further surgical step which targeting bore 18 aligned with the distal transverse bore 32 of the femur nail 22, To do this the clamping means of a sleeve 17 slid on the targeting arm (see FIG. 2) must be loosened so that the drill sleeve 24 can be changed from one targeting bore to another.

I claim:

1. A targeting device for an implant to be used for fractures comprising:
   (a) a head having a means for retaining a nail to be inserted into the medullary canal of a bone;
   (b) locking means for releasably fastening said nail to said means for retaining a nail; and
   (c) a targeting arm attached to said head, wherein said targeting arm has an axis and has a free end and extends substantially parallel to a nail attached to said means for retaining a nail and wherein said targeting arm has a plurality of first targeting bores for receiving a drill sleeve, said first targeting bores extending at different angles with respect to the axis of said targeting arm, wherein at least one of said targeting bores and at least one of said further targeting bores cross each other, such that the cross-section of one bore intersects the cross-section of another bore within said target arm.

2. The device of claim 1, wherein said plurality of first targeting bores extend at at least two different angles with respect to the axis of said targeting arm selected from the group consisting of 125°, 130°, 135°, and 140°.

3. The device of claim 1, wherein said first targeting bores are alignable with inclined proximal bores in a femur nail and wherein said targeting arm has at least one further targeting bore alignable with a distal bore in said femur nail.

4. The device of claim 1, wherein said targeting arm has a clamping slot parallel to said axis of said targeting arm, starting from said free end of said targeting arm and crossing said first targeting bores.

5. The device of claim 4, wherein said clamping slot extends only along a portion of the cross section of said targeting arm.

6. The device of claim 1, and including also a sleeve to be pushed onto said targeting arm in the area of said first targeting bores, said sleeve having a first wall portion to be interlocked with a second wall portion under a bias force, so that said first wall portion presses together cross-sectional portions of said targeting arm on either side of said clamping slot and wherein said sleeve has through-bores corresponding to said first targeting bores.

7. The device of claim 6, wherein said targeting arm has an approximately rectangular cross section, said sleeve has a mating box-like profile, said first wall portion and said second wall portion extend substantially perpendicular to each other, said first wall portion is bent away from the center of said sleeve, and the free end of said first wall portion cooperates with a projection of said second wall portion for locking.

8. The device of claim 7, and including also a plurality of sleeves to be pushed onto said targeting arm in the area of said first targeting bores, each sleeve having a plurality of through-bores for one of a number of different first targeting bores of said targeting arm.

9. The device of claim 1, wherein said head and said targeting arm are fixedly interconnected by a retaining bend of a material transparent to x-rays.

10. The device of claim 1, wherein said head and said targeting arm are made of light metal, preferably of an aluminum or titanium alloy.

11. The device of claim 1, wherein two parallel guide bores located in said head approximately perpendicular to said nail are provided for receiving Kirschner-wires extending laterally beyond said targeting arm for x-ray position control.

* * * * *